(12) United States Patent
Thomas et al.

(10) Patent No.: US 10,560,552 B2
(45) Date of Patent: Feb. 11, 2020

(54) COMPRESSION AND TRANSMISSION OF GENOMIC INFORMATION

(71) Applicant: NOBLIS, INC., Falls Church, VA (US)

(72) Inventors: Sterling Thomas, Falls Church, VA (US); Nate Dellinger, Falls Church, VA (US); Mychal Ivancich, Falls Church, VA (US)

(73) Assignee: NOBLIS, INC., Reston, VA (US)

( * ) Notice: Subject to any disclaimer, the term of this patent is extended or adjusted under 35 U.S.C. 154(b) by 215 days.

(21) Appl. No.: 14/718,950

(22) Filed: May 21, 2015

(65) Prior Publication Data

US 2016/0344849 A1 Nov. 24, 2016

(51) Int. Cl.
  *H04L 29/06* (2006.01)
  *H03M 7/30* (2006.01)
  *G16B 30/00* (2019.01)
(52) U.S. Cl.
  CPC .............. *H04L 69/04* (2013.01); *G16B 30/00* (2019.02); *H03M 7/30* (2013.01)
(58) Field of Classification Search
  None
  See application file for complete search history.

(56) References Cited

U.S. PATENT DOCUMENTS

| | | |
|---|---|---|
| 5,994,068 A | 11/1999 | Guilfoyle et al. |
| 6,141,657 A | 10/2000 | Rothberg et al. |
| 6,280,948 B1 | 8/2001 | Guilfoyle et al. |

(Continued)

FOREIGN PATENT DOCUMENTS

| | | |
|---|---|---|
| CA | 2036946 | 10/2001 |
| CN | 102682226 | 9/2012 |

(Continued)

OTHER PUBLICATIONS

Ateet Mehta and Bankim Patel. DNA Compression using hash based data structure. International Journal of Information Technology and Knowledge management. Jul.-Dec. 2010, vol. 2, No. 2, pp. 383-386.*

(Continued)

*Primary Examiner* — Olivia M. Wise
(74) *Attorney, Agent, or Firm* — Morrison & Foerster LLP

(57) ABSTRACT

Systems and methods for performing genomic information compression, transmission, and decompression are provided. A system for compression, transmission, and decompression of genomic information includes a first computer associated with a first index and a second computer associated with a second index, each index containing reference permutations of nucleic acid sequence portions, each permutation associated with a reference number. The first computer uses input genomic information and the first index to produce a compressed representation of the genomic information, and transmits the compressed representation to the second computer. The second computer uses the compressed representation and the second index to assemble a data representation of the genomic information. The compressed representation comprises references to permutations, indications of locations of each permutation in the input information, indications of variations to permutations, and/or indications of sequence length.

22 Claims, 5 Drawing Sheets

Specification includes a Sequence Listing.

(56) References Cited

U.S. PATENT DOCUMENTS

| | | | |
|---|---|---|---|
| 8,209,130 | B1 | 6/2012 | Kennedy et al. |
| 8,812,243 | B2 * | 8/2014 | Cardonha ............... G06F 19/22 702/19 |
| 2002/0058256 | A1 | 5/2002 | Rothberg et al. |
| 2004/0002816 | A1 | 1/2004 | Milosavljevic |
| 2004/0048264 | A1 | 3/2004 | Stoughton et al. |
| 2004/0053246 | A1 | 3/2004 | Sorenson |
| 2004/0224330 | A1 | 11/2004 | He |
| 2005/0239102 | A1 | 10/2005 | Verdine et al. |
| 2006/0112264 | A1 | 5/2006 | Agarwal |
| 2006/0286566 | A1 | 12/2006 | Lapidus et al. |
| 2007/0016612 | A1 | 1/2007 | James et al. |
| 2008/0168572 | A1 | 7/2008 | Stetter et al. |
| 2009/0055425 | A1 | 2/2009 | Evans et al. |
| 2009/0233802 | A1 | 9/2009 | Bignell et al. |
| 2009/0270277 | A1 * | 10/2009 | Glick ..................... G06F 19/22 506/24 |
| 2009/0292665 | A1 | 11/2009 | Den Hartog |
| 2010/0287165 | A1 | 11/2010 | Halpern et al. |
| 2011/0103501 | A1 | 5/2011 | Khojastepour et al. |
| 2011/0257889 | A1 | 10/2011 | Klammer et al. |
| 2011/0264377 | A1 | 10/2011 | Cleary |
| 2011/0295858 | A1 | 12/2011 | Ahn et al. |
| 2012/0016658 | A1 | 1/2012 | Wu et al. |
| 2013/0268206 | A1 | 10/2013 | Porreca et al. |
| 2013/0338934 | A1 | 12/2013 | Asadi et al. |
| 2014/0075183 | A1 * | 3/2014 | Wang ..................... G06F 19/22 713/150 |
| 2014/0358937 | A1 | 12/2014 | Thomas et al. |
| 2016/0306919 | A1 * | 10/2016 | Ding ....................... G06F 19/18 |
| 2018/0330053 | A1 | 11/2018 | Ivancich et al. |
| 2019/0146962 | A1 | 5/2019 | Thomas et al. |

FOREIGN PATENT DOCUMENTS

| | | |
|---|---|---|
| WO | 94/01582 | 1/1994 |
| WO | 01/098535 A2 | 12/2001 |
| WO | 2007/137225 A2 | 11/2007 |
| WO | 2008/000090 A1 | 1/2008 |
| WO | 2010/104608 A2 | 9/2010 |
| WO | 2012/168815 A2 | 12/2012 |

OTHER PUBLICATIONS

Ning et al. SSAHA: A Fast Search Method for Large DNA Databases. Genome Research, vol. 11, No. 10, p. 1725-1729 (Year: 2001).*

Munoz-Torres et al. Hymenoptera Genome Database: integrated community resources for insect species of the order Hymenoptera. Nucleic Acids Research, vol. 39, Issue suppl_1, pp. D658-D662 (Year: 2011).*

International Search Report and Written Opinion dated Sep. 7, 2016, directed to International Application No. PCT/US2016/033786; 9 pages.

Flicek et al. (Nov. 2009). "Sense from Sequence Reads: Methods for Alignment and Assembly," Nature Methods Supplement 6(11): 6-12; Corrigendum: 1.

Hancock-Hanser et al. (2013). "Targeted Multiplex Next-Generation Sequencing: Advances in Techniques of Mitochondrial and Nuclear DNA Sequencing for Population Genomics," Molecular Ecology Resources 13: 254-268.

Li et al. (Jun. 1, 2009). "SNP Detection for Massively Parallel Whole-Genome Resequencing," Genome Research 19: 1124-1132.

Office Action dated Oct. 19, 2017, directed to Chinese Application No. 201410228956.7; 10 pages.

Ossowski et al. (Oct. 3, 2008). "Sequencing of Natural Strains of *Arabidopsis thaliana* with Short Reads," Genome Research 18: 2024-2033.

Search Report dated May 7, 2015, directed to European Application No. 14170198.7, 17 pages.

Thomas et al., U.S. Office Action dated Dec. 29, 2016, directed to U.S. Appl. No. 13/904,738; 23 pages.

Thomas et al., U.S. Office Action dated Jan. 28, 2015, directed to U.S. Appl. No. 13/904,738; 17 pages.

Thomas et al., U.S. Office Action dated Jun. 27, 2018, directed to U.S. Appl. No. 13/904,738; 32 pages.

Thomas et al., U.S. Office Action dated Mar. 24, 2016, directed to U.S. Appl. No. 13/904,738; 21 pages.

Thomas et al., U.S. Office Action dated May 28, 2015, directed to U.S. Appl. No. 13/904,738; 22 pages.

Thomas et al., U.S. Office Action dated Nov. 1, 2017, directed to U.S. Appl. No. 13/904,738; 24 pages.

Tsaftaris et al. (2007). "Retrieval Accuracy of Very Large DNA-Based Databases of Digital Signals," European Signal Processing Conference (EUSIPCO):1561-1565.

* cited by examiner

COMPRESSION AND TRANSMISSION OF GENOMIC INFORMATION

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 739642000400SEQLIST.TXT, date recorded: Jul. 10, 2015, size: 5 KB).

FIELD

This relates to systems and methods for storage and transmission of genomic information.

BACKGROUND

Advancement of gene sequencing technology is allowing for genomic information to be more rapidly and readily processed by faster gene sequencing methods. Genomic information often includes very large amounts of data; for example, a human genome may be represented by about 200 GB of data. Even much simpler genomes, such as those of bacteria, may still be represented by several GB of data. The Ebola genome, for example, may be represented by about 1 GB of data, while the *E. coli* genome may be represented by about 5 GB of data.

When genomic information, such as a gene sequence, is derived at one location, it often must be shared with third parties at other locations. Current methods for transferring genomic information from one location to another location include physically transporting computer-readable storage media, such as hard drives, from one location to another. Current methods are cumbersome because they depend on transmitting and/or transporting large amounts of data, such as data representing entire genome sequences. Transmitting and/or transporting such large amounts of data is time-consuming and expensive, and uses large amounts of processing power and network bandwidth.

SUMMARY OF THE INVENTION

Accordingly, there is a need for methods and systems for compressing and transmitting genomic information. Such methods and systems may enable newly-sequenced genomes to be shared with remote locations quickly and efficiently, immediately upon their sequencing. Hardware and software infrastructure is needed to store indexes used for compression of genomic information, to receive input genomic information, to determine and store compressed representations in accordance with the input information and a first index, to transmit the compressed representation, to receive the compressed representation, and to decompress the compressed representation with reference to a second index to create a data representation of the genomic information. Efficient compression, transmission, and decompression of genomic information may be achieved by providing multiple instances of a reference index in multiple locations, the instances of the reference index each containing elements corresponding to reference permutations of nucleic acid sequence portions, and using one instance of the index to compress genomic information and the other to decompress genomic information. Providing the instances of the index before the compression and transmission of the genomic information may obviate the need to send large amounts of data, such as permutations of nucleic acid sequences, from one location to another.

In some embodiments, a method for communicating genomic information comprises: receiving information comprising input data representing a nucleic acid sequence, the input data comprising a plurality of portions; identifying, for each of the plurality of portions, an element in an index that corresponds to the respective portion, wherein the index comprises a plurality of elements corresponding to reference permutations of nucleic acid sequence portions; determining, for each of the plurality of portions, a position in the nucleic acid sequence of the respective portion; storing, for each of the plurality of portions, as part of a compressed representation of the nucleic acid sequence, information comprising a reference to the respective determined element, and information indicating the determined position of the respective portion; and transmitting the compressed representation of the nucleic acid sequence over a computer network.

In some embodiments, a method of receiving genomic information comprises: receiving a compressed representation of a nucleic acid sequence over a computer network; identifying, in accordance with each of a plurality of references in the compressed representation, a corresponding respective element in an index, wherein the index comprises a plurality of elements corresponding to reference permutations of nucleic acid sequences portions; determining, in accordance with each of a plurality of indicators in the compressed representation, a respective position in the assembled data representation for each identified element; and assembling a data representation of the nucleic acid sequence by inserting each identified element at the corresponding determined position.

In some embodiments, a method for communicating genomic information comprises, at a first computer associated with a first index, wherein the first index comprises a first plurality of elements corresponding to reference permutations of nucleic acid sequence portions: receiving information comprising input data representing a nucleic acid sequence, the input data comprising a plurality of portions; identifying, for each of the plurality of portions, an element in the first index that corresponds to the respective portion; determining, for each of the plurality of portions, a position in the nucleic acid sequence of the respective portion; storing, for each of the plurality of portions, as part of a compressed representation of the nucleic acid sequence information comprising a reference to the respective determined element, and information indicating the determined position of the respective portion; and transmitting the compressed representation of the nucleic acid sequence over a computer network. In some embodiments, the method further comprises, at a second computer associated with a second index, wherein the second index comprises a second plurality of elements corresponding to reference permutations of nucleic acid sequence portions: receiving the compressed representation of the nucleic acid sequence over the computer network; identifying, in accordance with each of the plurality of references in the compressed representation, a corresponding respective element in the second index; determining, in accordance with each of a plurality of indicators in the compressed representation, a respective position in the assembled data representation for each identified element; and assembling a data representation of the nucleic acid sequence by inserting each identified element at the corresponding determined position.

In some embodiments, a system for communicating genomic information comprises: a first computer having a memory having stored thereon a first index, the first index comprising a first plurality of elements corresponding to reference permutation of nucleic acid sequence portions; a second computer having a memory having stored thereon a second index, the second index comprising a second plurality of elements corresponding to reference permutations of nucleic acid sequence portions; a network enabling data to be transferred from the first computer to the second computer; and a first processor associated with the first computer. In some embodiments, the first processor is configured to, at a first computer associated with a first index, wherein the first index comprises a first plurality of elements corresponding to reference permutations of nucleic acid sequence portions: receive information comprising input data representing a nucleic acid sequence, the input data comprising a plurality of portions; identify, for each of the plurality of portions, an element in the first index that corresponds to the respective portion; determine, for each of the plurality of portions, a position in the nucleic acid sequence of the respective portion; store, for each of the plurality of portions, as part of a compressed representation of the nucleic acid sequence information comprising a reference to the respective determined element, and information indicating the determined position of the respective determined portion; and transmit the compressed representation of the nucleic acid sequence over a computer network. In some embodiments, the system further comprises a second processor associated with the second computer, the second processor configured to: receive the compressed representation of the nucleic acid sequence over the computer network; identify, in accordance with each of the plurality of references in the compressed representation, a corresponding respective element in the second index; determine, in accordance with each of a plurality of indicators in the compressed representation, a respective position in the assembled data representation for each identified element; and assemble a data representation of the nucleic acid sequence by inserting each identified element at the corresponding determined position.

In some embodiments, a non-transitory computer-readable storage medium comprises instructions for: receiving information comprising input data representing a nucleic acid sequence, the input data comprising a plurality of portions; identifying, for each of the plurality of portions, an element in an index that corresponds to the respective portion, wherein the index comprises a plurality of elements corresponding to reference permutations of nucleic acid sequence portions; determining, for each of the plurality of portions, a position in the nucleic acid sequence of the respective portion; storing, for each of the plurality of portions, as part of a compressed representation of the nucleic acid sequence, information comprising a reference to the respective determined element, and information indicating the determined position of the respective portion; and transmitting the compressed representation of the nucleic acid sequence over a computer network.

In some embodiments, a non-transitory computer-readable storage medium comprises instructions for: receiving a compressed representation of a nucleic acid sequence over a computer network; identifying, in accordance with each of a plurality of references in the compressed representation, a corresponding respective element in an index, wherein the index comprises a plurality of elements corresponding to reference permutations of nucleic acid sequences portions; determining, in accordance with each of a plurality of indicators in the compressed representation, a respective position in the assembled data representation for each identified element; and assembling a data representation of the nucleic acid sequence by inserting each identified element at the corresponding determined position.

In some embodiments, a non-transitory computer-readable storage medium comprises instructions for, at a first computer associated with a first index, wherein the first index comprises a first plurality of elements corresponding to reference permutations of nucleic acid sequence portions: receiving information comprising input data representing a nucleic acid sequence, the input data comprising a plurality of portions; identifying, for each of the plurality of portions, an element in the first index that corresponds to the respective portion; determining, for each of the plurality of portions, a position in the nucleic acid sequence of the respective portion; storing, for each of the plurality of portions, as part of a compressed representation of the nucleic acid sequence information comprising a reference to the respective determined element, and information indicating the determined position of the respective portion; and transmitting the compressed representation of the nucleic acid sequence over a computer network. In some embodiments, the non-transitory computer-readable storage medium further comprises instructions for, at a second computer associated with a second index, wherein the second index comprises a second plurality of elements corresponding to reference permutations of nucleic acid sequence portions: receiving the compressed representation of the nucleic acid sequence over the computer network; identifying, in accordance with each of the plurality of references in the compressed representation, a corresponding respective element in the second index; determining, in accordance with each of a plurality of indicators in the compressed representation, a respective position in the assembled data representation for each identified element; and assembling a data representation of the nucleic acid sequence by inserting each identified element at the corresponding determined position.

In some embodiments, a device comprises: one or more processors; memory; and one or more programs, wherein the one or more programs are stored in the memory and configured to be executed by the one or more processors. In some embodiments, the one or more programs include instructions for: receiving information comprising input data representing a nucleic acid sequence, the input data comprising a plurality of portions; identifying, for each of the plurality of portions, an element in an index that corresponds to the respective portion, wherein the index comprises a plurality of elements corresponding to reference permutations of nucleic acid sequence portions; determining, for each of the plurality of portions, a position in the nucleic acid sequence of the respective portion; storing, for each of the plurality of portions, as part of a compressed representation of the nucleic acid sequence, information comprising a reference to the respective determined element, and information indicating the determined position of the respective portion; and transmitting the compressed representation of the nucleic acid sequence over a computer network.

In some embodiments, a device comprises: one or more processors; memory; and one or more programs, wherein the one or more programs are stored in the memory and configured to be executed by the one or more processors. In some embodiments, the one or more programs includes instructions for: receiving a compressed representation of a nucleic acid sequence over a computer network; identifying, in accordance with each of a plurality of references in the compressed representation, a corresponding respective element in an index, wherein the index comprises a plurality of elements corresponding to reference permutations of nucleic acid sequences portions; determining, in accordance with each of a plurality of indicators in the compressed representation, a respective position in the assembled data representation for each identified element; and assembling a data representation of the nucleic acid sequence by inserting each identified element at the corresponding determined position.

DETAILED DESCRIPTION OF THE INVENTION

The following description sets forth exemplary methods, parameters and the like. It should be recognized, however, that such description is not intended as a limitation on the scope of the present disclosure but is instead provided as a description of exemplary embodiments.

Below, FIGS. 1-4 provide a description of exemplary systems and methods for performing the techniques for genomic information compression, transmission, and decompression disclosed herein.

Although the following description uses terms first, second, etc. to describe various elements, these elements should not be limited by the terms. These terms are only used to distinguish one element from another.

The terminology used in the description of the various described embodiments herein is for the purpose of describing particular embodiments only and is not intended to be limiting. As used in the description of the various described embodiments and the appended claims, the singular forms "a", "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

The term "if" may be construed to mean "when" or "upon" or "in response to determining" or "in response to detecting," depending on the context. Similarly, the phrase "if it is determined" or "if [a stated condition or event] is detected" may be construed to mean "upon determining" or "in response to determining" or "upon detecting [the stated condition or event]" or "in response to detecting [the stated condition or event]," depending on the context.

Figure 1:
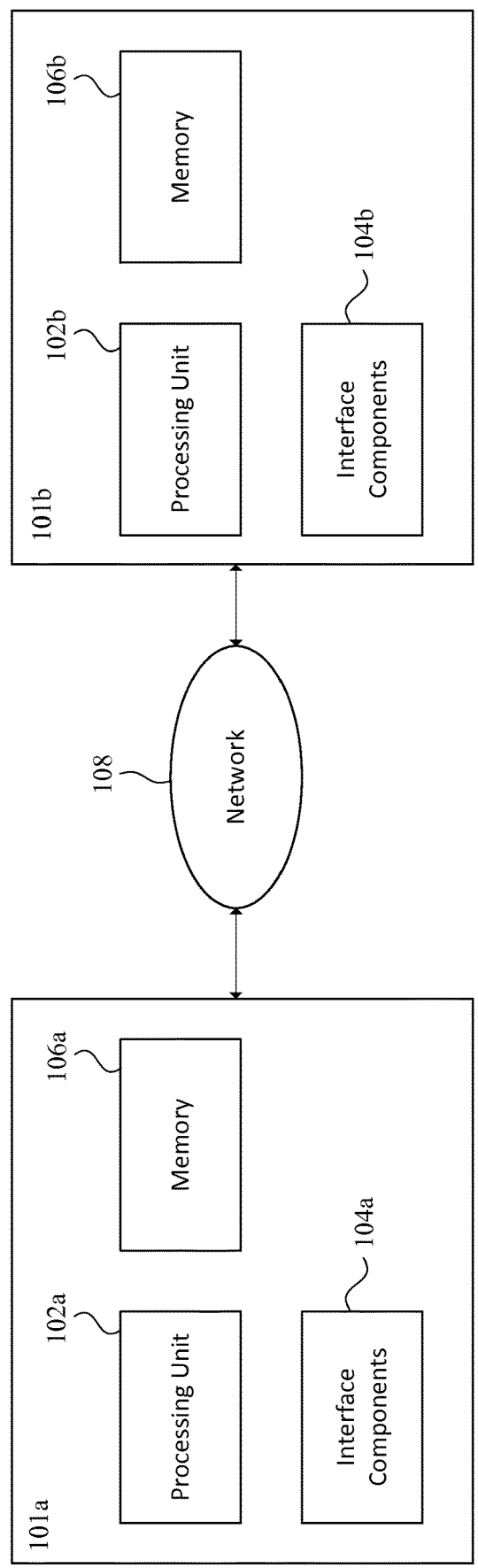
FIG. 1 is a block diagram of a computing system.

FIG. 1 shows an exemplary system that is configured to perform one or more software processes that, when executed, provide one or more aspects of the disclosed embodiments. FIG. 1 is not intended to be limiting to the disclosed embodiment as the components used to implement the processes and features disclosed herein may vary.

In accordance with certain disclosed embodiments, a computing system 100 may be provided that includes computers 101a and 101b and network 108. Other components known to one of ordinary skill in the art may be included in system 100 to process, transmit, provide, and receive information consistent with the disclosed embodiments. In some embodiments, network 108 may be provided in addition to, or replaced by, any other suitable communication channel enabling communicating information between computers 101a and 101b, including any additional public or private network, any direct or indirect wired or wireless data connection, or any means of storing and/or physically transporting data.

Computer 101a may include computer system components, such as one or more servers, desktop computers, workstations, tablets, hand held computing devices, memory devices, and/or internal network(s) connecting the components. In one embodiment, computer 101a may be a server that includes one or more processors, memory devices, and interface components 104a. For example, computer 101a may include processing unit 102a, memory 106a, and interface components 104a. Computer 101a may be a single server or may be configured as a distributed computer system including multiple servers or computers that interoperate to perform one or more of the processes and functionalities associated with the disclosed embodiments.

Processing unit 102a may include one or more known processing devices, such as a microprocessor from the Pentium™ family manufactured by Intel™ or the Turion™ family manufactured by AMD™. Processing unit 102a may include a single core or multiple core processor system that provides the ability to perform parallel processes simultaneously. For example, processing unit 102a may include a single core processor that is configured with virtual processing technologies known to those skilled in the art. In certain embodiments, processing unit 102a may use logical processors to simultaneously execute and control multiple processes. The one or more processors in processing unit 102a may implement virtual machine technologies, or other similar known technologies to provide the ability to execute, control, run, manipulate, store, etc. multiple software processes, applications, programs, etc. In another embodiment, processing unit 102a may include a multiple-core processor arrangement (e.g., dual or quad core) that is configured to provide parallel processing functionalities to allow electronic computing system 100 to execute multiple processes simultaneously. One of ordinary skill in the art would understand that other types of processor arrangements, such as those used in Cray supercomputers, could be implemented that provide for the capabilities disclosed herein.

In some embodiments, computer 101a may be a supercomputer, such as the Cray XMT or Cray XMT 2. Supercomputers may include multiple-core processor arrangements paired with a memory that are configured to provide greater parallel processing functionalities relative to consumer-grade desktop computers, laptops, and the like. The Cray XMT, for example, may include 128 TB (terabytes) of memory and processor cores capable of executing up to 8,192 threads in parallel. Similarly, the Cray XMT 2 may include 512 TB of memory and 128 processor cores, with each processor core capable of executing 128 threads, for a total of 16,384 threads.

In some embodiments, computer 101a may be a consumer-grade desktop computer, laptop computer, tablet, cell phone, or the like.

Computer 101a may include one or more storage devices configured to store information used by processing unit 102a (or other components) to perform certain functions related to the disclosed embodiments. In one example, memory 106a may include instructions to enable the one or more processors in processing unit 102a to execute one or more applications, such as server applications, network communication processes, and any other type of application or software known to be available on computer systems. Alternatively, the instructions, application programs, etc. may be stored in an external storage or available from a memory over network 108. The one or more storage devices may be a volatile or non-volatile, magnetic, semiconductor, tape, optical, removable, non-removable, or other type of storage device or tangible computer-readable medium.

In some embodiments, memory 106a may include instructions that, when executed by the one or more processors in processing unit 102a, perform one or more processes consistent with the functionalities disclosed herein. Methods, systems, and articles of manufacture consistent with disclosed embodiments are not limited to separate programs or computers configured to perform dedicated tasks. For example, computer 101a may include a memory that may include one or more programs to perform one or more functions for creating, transmitting, receiving, and/or decompressing a compressed representation of genomic information, including as described in the disclosed embodiments. Moreover, the one or more processors in processing unit 102a may execute one or more programs located remotely from system 100. For example, system 100 may access one or more remote programs, that, when executed, perform functions related to disclosed embodiments. Memory 106a may include one or more memory devices that store data and instructions used to perform one or more features of the disclosed embodiments. Memory 106a may also include any combination of one or more databases controlled by memory controller devices (e.g., server(s), etc.) or software, such as document management systems, Microsoft SQL databases, SharePoint databases, Oracle™ databases, Sybase™ databases, or other relational databases.

Computer 101a may also be communicatively connected to one or more memory devices (e.g., databases (not shown)) locally or through network 108. The remote memory devices may be configured to store information and may be accessed and/or managed by computer 101a. By way of example, the remote memory devices may be document management systems, Microsoft SQL databases, SharePoint databases, Oracle™ databases, Sybase™ databases, or other relational databases. Systems and methods of disclosed embodiments, however, are not limited to separate databases or even to the use of a database.

Computer 101a may also include one or more I/O devices that may comprise one or more interfaces for receiving signals or input from input devices and providing signals or output to one or more output devices that allow data to be received and/or transmitted by electronic computing system 100. For example, interface components 104a may provide interfaces to one or more input devices, such as one or more keyboards, mouse devices, and the like, that enable computer 101a to receive data from one or more users. Further, interface components 104a may include components configured to send and receive information between components of computer 101a or external to computer 101a, such as network 108.

In some embodiments, the foregoing description of computer 101a may be additionally applicable to computer 101b, such that computer 101b may share some or all of the traits of computer 101a.

Network 108 may be any type of network that provides communications, exchanges information, and/or facilitates the exchange of information between computer 101a and computer 101b and other computing systems. In one embodiment, network 108 may be the Internet, a Local Area Network, or other suitable connection(s) that enables computers 101a and/or 101b to send and/or receive information between the components of system 100.

One or both of computer 101a and computer 101b may create, receive, store, and/or provide an index of a nucleic acid sequence or an amino acid sequence. The index may include a plurality of elements, with each element corresponding to a permutation of a nucleic acid sequence or an amino acid sequence (or another type of sequence). Computer 101a and/or 101b may implement the index using a variety of data structures, such as databases, matrices, arrays, linked lists, trees, and the like. The choice of data structures may vary and is not critical to any embodiment. Computer 101a may store the index in memory 106a. More specifically, the index may be stored on hard disk; computer 101a and/or computer 101b may also load the index into RAM for increased performance.

An example nucleic acid sequence is shown in Table 1, below.

TABLE 1

Example Nucleic Acid Sequence

1234568790123456879012345687901234568790

ATTGCTTCCATGGGTC  (SEQ ID NO: 17)

As shown in Table 1, a nucleic acid sequence contains various combinations of the bases adenine, guanine, thymine, and cytosine, represented by the letters "A," "G," "T," and "C," respectively. The numerical digits included in Table 1 enable convenient identification of the positions of the different bases appearing in the sequence. For example, the base adenine appears in positions 1 and 10 of the sequence appearing in Table 1, which is 16 bases in length.

An example amino acid sequence is shown in Table 2, below.

TABLE 2

Example Amino Acid Sequence

1234567890123456789012345678901234568790

DVQMIQSPSSLSASLGDIVTMTCQASQGTSINLNWFQQKP

GKAPKLLIYGSSNLEDGVPSRFSGSRYGTDFTLTISSLED

EDLATYFCLQHSYLPYTFGGGTKLEIKR (SEQ ID NO: 18)

As shown in Table 2, an amino acid sequence may contain various combinations of the bases, as represented by the one-letter abbreviations for the standard amino acids. The amino acid sequence shown in Table 2 recites amino acids selected from the 22 standard (proteinogenic or natural) amino acids, but sequences comprising nonstandard amino acid sequences may also be used.

Figure 2:
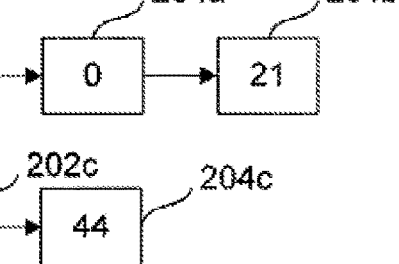
FIG. 2 is a block diagram of an index of reference permutations of nucleic acid sequence portions. The first segment of the nucleic sequence 206 is SEQ ID NO: 1; the second segment of the nucleic sequence 206 is SEQ ID NO: 2. The sequence at position "0" is SEQ ID NO: 3; the sequence at position "1" is SEQ ID NO: 4; the sequence at position "2" is SEQ ID NO: 5; and the sequence at position "3" is SEQ ID NO: 6. The sequence at position "n" is SEQ ID NO: 1; the sequence at position "n+1" is SEQ ID NO: 7; the sequence at position "n+2" is SEQ ID NO: 8. The sequence at position "4k−4" is SEQ ID NO: 9; the sequence at position "4k−3" is SEQ ID NO: 10; the sequence at position "4k−2" is SEQ ID NO: 11; the sequence at position "4k−1" is SEQ ID NO: 12.

FIG. 2 illustrates an index 200 of a nucleic acid sequence, consistent with some embodiments disclosed herein. Although FIG. 2 illustrates use of nucleic acid sequences, one of ordinary skill in the art would understand how such an example would apply to other types of sequences, such as RNA sequences (e.g., involving the bases adenine, guanine, uracil, and cytosine), sequences of artificially synthesized polymers (such as PNA), and amino acid sequences, including standard (proteinogeneic or natural) and non-standard (non-proteinogenic or non-natural) amino acids.

As shown in FIG. 2, index 200 includes a plurality of elements corresponding to various permutations of nucleic acid sequences. In the case of FIG. 2, each permutation is 16 bases in length, resulting in an index with $4^{16}$ or 4,294,967,296 elements (note that each base of a nucleic acid sequence is one of four types). More generally, the size or the number of elements of index 200 is equal to $4^k$, where k is the length, in bases, of each permutation.

As shown to the left of each element in FIG. 2, a given element of the index may be referred to by its position number. For example, as illustrated in FIG. 2, position "0" refers to the element corresponding to the permutation "AAAAAAAAAAAAAAAA" (which is also indicated by reference number 202a (SEQ ID NO: 3)), position "3" refers to the element corresponding to the permutation "AAAAAAAAAAAAAATT," (SEQ ID NO: 6), and position "n" refers to the element corresponding to the permutation "GTAAGATCCGCTACAA" (which is also indicated by reference number 202b (SEQ ID NO: 1)). Because the index may have up to $4^k$ elements, as described above, the elements may be referenced beginning from position "0" to position "$4^{k-1}$."

In some embodiments, index 200 may contain a number of elements fewer than the number of possible permutations of sequences of a predetermined length. For instance, computer 101a and/or 101b may use statistical and/or probabilistic methods to reduce the number of elements so that only certain nucleic acid sequences (e.g., those most likely to occur) are included in the index. Such an index has the potential advantage of increased computational efficiency and reduction in memory requirements.

Continuing on, reference numbers 202a, 202b, 202c, and 202d of FIG. 2 represent different elements (e.g., elements "0," "n," "n+2," and "$4^{k-1}$," respectively) appearing in index 200. In some embodiments, reference numbers 204a, 204b, and 204c describe additional features of index 200. In particular, these reference numbers indicate position data corresponding to certain elements of the index, e.g., reference numbers 204a and 204b indicate position data stored in element 202b, and reference number 204c indicates position data stored in element 202c. In some embodiments, such as those in which the index includes reference numbers 204 or other position data, the index may provide information about one or more specific nucleic acid sequences; thus, the position data stored in an element may reflect a position or location of the nucleic acid sequence in which the corresponding permutation occurs. For instance, as shown in FIG. 2, reference numbers 204a and 204b indicate that the permutation corresponding to element n of the index, "GTAAGATCCGCTACAA," (SEQ ID NO: 1), appears beginning at positions "0" and "21" of the nucleic acid sequence 206. Similarly, reference number 204c indicates that the permutation corresponding to element n+2 of the index, "GTAAGATCCGCTACTA," (SEQ ID NO: 8), appears beginning at position "44" of the nucleic acid sequence 206.

The nucleic acid elemental sequences may be received from an underlying nucleic acid sample sequence, which may be much greater in length (e.g., millions or billions of bases).

Figure 3:
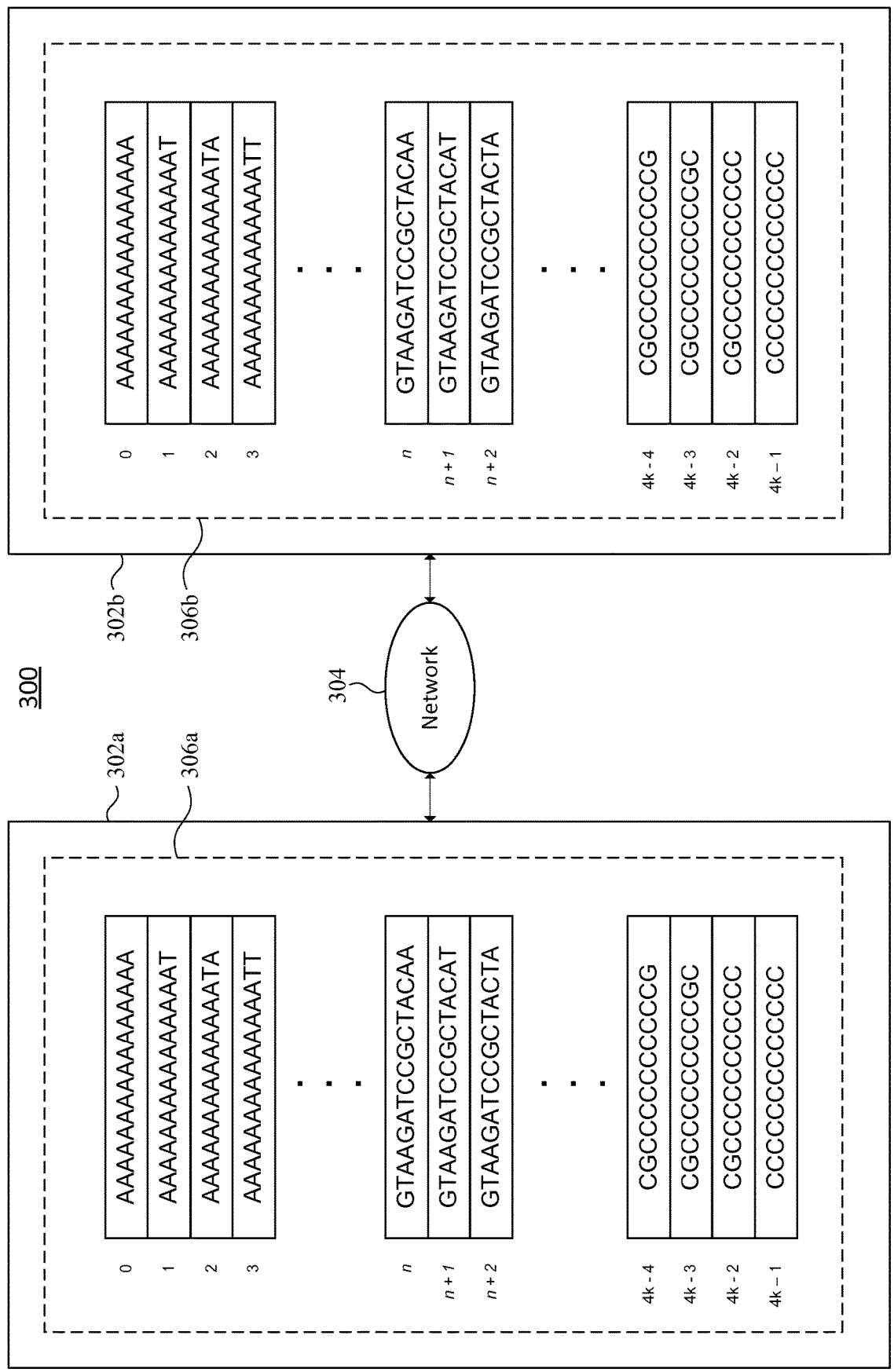
FIG. 3 is a block diagram of a computing system storing indexes of indexes of reference permutations of nucleic acid sequence portions. The sequence at position "0" of indexes 306a and 306b is SEQ ID NO: 3; the sequence at position "1" of indexes 306a and 306b is SEQ ID NO: 4; the sequence at position "2" of indexes 306a and 306b is SEQ ID NO: 5; and the sequence at position "3" of indexes 306a and 306b is SEQ ID NO: 6. The sequence at position "n" of indexes 306a and 306b is SEQ ID NO: 1; the sequence at position "n+1" of indexes 306a and 306b is SEQ ID NO: 7; the sequence at position "n+2" of indexes 306a and 306b is SEQ ID NO: 8. The sequence at position "4k−4" of indexes 306a and 306b is SEQ ID NO: 13; the sequence at position "4k−3" of indexes 306a and 306b is SEQ ID NO: 14; the sequence at position "4k−2" of indexes 306a and 306b is SEQ ID NO: 15; the sequence at position "4k−1" of indexes 306a and 306b is SEQ ID NO: 16.

FIG. 3 illustrates a system 300 that may be useful in efficiently transferring genomic information. The system comprises computers 302a and 302b, which are interconnected by network 304. In some embodiments, the system is system 100 as described above with reference to FIG. 1, and computers 302a and 302b are computers 101a and 101b, respectively, and network 304 is network 108.

System 300 further comprises two instances of an index, indexes 306a and 306b. In some embodiments, one or more of the indexes 306a and 306b of the index share one or more characteristics of the index 200 described above with reference to FIG. 2. In some embodiments, one of more of the indexes 306a and 306b are stored on memories of computers 302a and 302b, respectively, such as memories 106a and 106b. In some embodiments, one or more of the indexes 306a and 306b are stored in any other suitable local or remote storage, including memories or databases that are accessible by either or both of computers 302a and 302b through network 304.

In some embodiments, one of more of indexes 306a and 306b may, unlike index 200 shown above in FIG. 2, not contain any location information such as reference numbers 204 and may not contain other information that is specifically related to a particular nucleic acid sequence. That is, in some embodiments, the indexes 306a and 306b may each be a generalized index that represents only the elements of the index and corresponding reference numbers 202, such as elements "AAAAAAAAAAAAAAAA" (SEQ ID NO: 3) through "CCCCCCCCCCCCCCCC" (SEQ ID NO: 12) and the corresponding reference numbers 0 through $4^{k-1}$. In some embodiments, the indexes 306a and 306b may each contain an exhaustive listing of every mathematically possible permutation of bases for one or more given element-lengths k, representing every mathematically possible element of the given length(s) and corresponding reference numbers. In some embodiments, one or more of the indexes 306 may contain less than every mathematically possible permutation; for example, one or more of the indexes 306 may contain every practically possible permutation, such as by using probabilistic or historical data to select a subset of permutations that are likely to occur. In some embodiments, one or more of the indexes 306 may contain every practically possible, mathematically possible, or historically known permutation with respect to a certain species or group of species, such that permutations that will likely not be necessary to compress or decompress genomic information for a certain species or group of species may not be included in one or more of the indexes 306. In some embodiments, one or more of the indexes 306 may not include permutations that are not known to occur in nature.

In some embodiments, the elements may each be 16 bases in length and 128 bits in size, while the reference numbers may each be 8 bits in size. In some embodiments, the elements may be more or less than 16 bases in length and may be more or less than 128 bits in size. In some other embodiments, the elements may be shorter or longer, which will affect the overall size of each index, and will affect the number of elements that are necessary to represent a given sequence of a certain length. For example, in some embodiments, the elements may each be fewer than 16 bases in length, such as 12 or fewer bases in length, or 8 or fewer bases in length. In some embodiments, the elements may each be more than 16 bases in length, such as 20 or more bases in length, 24 or more bases in length, or 32 bases in length. Using bases comprising more or fewer bases affects the overall size of the index by affecting the size of each element and also the number of permutations $4^k$ that may be included in the index. An important consideration in choosing the number of bases in each index may be the overall storage capacity required to store an index comprised of bases of the chosen length; indexes of bases of a greater length may be require greater storage capacity.

In some other embodiments the elements may be comprised of more or less than four unique nucleotides. For example, some elements may contain a fifth wildcard base in addition to the four nucleotides A, T, C, and G. In such embodiments, $5^k$ elements (as opposed to only $4^k$ elements) are needed in order for an index to represent an exhaustive listing of all possible elements of length k. With elements of length 16, this would increase the number of elements from 4,294,967,296 to 152,587,890,625, representing about a 40-fold increase. With approximately 40 times more elements in such an index, approximately 40 times as much memory could be needed to accommodate such an index, and processing times for searching and navigating such an index could also be slowed.

In some embodiments, the indexes 306a and 306b are identical to one another, in that they contain all of the same elements in the same arrangement with the same corresponding reference numbers. In some embodiments, the only difference between the indexes 306a and 306b is the location at which they are stored. The two instances may thus represent the same index, simply stored at different locations in a computer system and/or at different geographic locations. In some embodiments, one of the indexes 306 may contain a subset of the same elements and corresponding reference numbers as the other index, such that a portion of the indexes, but not the entirety of the indexes, are identical. For example, one index may be truncated, containing only known or probable permutations, while the other index may contain all mathematically possible permutations.

By providing two indexes 306 which contain some or all of the same elements and corresponding reference numerals, the indexes 306 may be used as encoding and decoding indexes, such that (as will be explained further with respect to the method below) one index (e.g., 306a) may be used to encode or compress genomic information, and another index (e.g., 306b) may be used to decode or decompress the encoded or compressed genomic information. In this manner, providing the indexes 306 may enable for genomic information to be transmitted without requiring sending full-sized, uncompressed, or un-encoded data. In some embodiments, the indexes 306 may be provided at two or more locations in advance of any genomic information (uncompressed or otherwise) being provided at any of the locations. This may allow for a party or a location to be prepared to compress, send, receive, and/or decompress genomic information before the genomic information is available or present. It may also allow for a party or location to be equipped with the tools to compress, send, receive, and/or decompress genomic information without the party or location being provided with certain valuable proprietary information, such as genomic information that may not be provided at the time.

In some embodiments, an index 302 may be provided by way of physical transportation, such as being provided in a hard drive or in any other suitable computer memory. In some embodiments, an index 302 may be provided by way of wired or wireless network communication, such as transmission over a private network or over the internet. In some embodiments, an index 302 may be built on the computer (e.g., 101a, 101b, 302a, or 302b) on which it resides. For example, a program, application, or other computer instructions may be provided to a computer, allowing the computer to construct the index and store it. For example, an algorithm may be provided as part of a computer program that is provided over the internet, and the algorithm may enable a computer to form and store an index such as either of indexes 306.

In some embodiments, more than one index may be provided in the same computer system or at the same location or to the same party. For example, one index containing elements of length 16 may be provided, and another index containing elements of length 12 may be provided. In some embodiments, one index may contain both elements of length 16 and of length 12, or of any two or more element lengths $k_1$, $k_2$, etc. In some embodiments, such an index may be capable of compressing and/or decompressing genomic information with respect to a compression method using elements of length $k_1$, $k_2$, $k_n$, etc., or any combination thereof. In some embodiments, one or more of the indexes 306 may include multiple sets of reference numbers that allow the index to function as if it were an index containing multiple sets of elements of different lengths k. For example, an index containing $4^{16}$ elements of length 16 may contain every mathematically possible permutation of elements with 16 bases where the bases are either A, G, T, or C. That exhaustive set of $4^{16}$ bases may be understood, however, as itself containing the complete set all $4^{12}$ mathematically possible permutations of elements of length 12 where the bases are either A, G, T, or C. By taking the first 12 bases (or any given contiguous portion of length 12) of each of the 16-base elements, for example, the leading 12 bases of $4^{12}$ of the $4^{16}$ bases may account for an exhaustive set of all $4^{12}$ mathematically possible permutations of elements of length 12. Thus, the $4^{12}$ elements that account for the permutations of elements of length 12 may be assigned, in some embodiments, a second reference number that indicates an element's first 12 bases as being a given permutation. In this manner, by adding just $4^{12}$ (under 17 million) reference numerals to an index having $4^{16}$ (over 4 billion) reference numerals and $4^{16}$ elements, the index may serve as two indexes for compressing and/or decompressing genomic information using elements of 16 and/or 12 bases in length.

Compression and Transmission Method

Figure 4A:
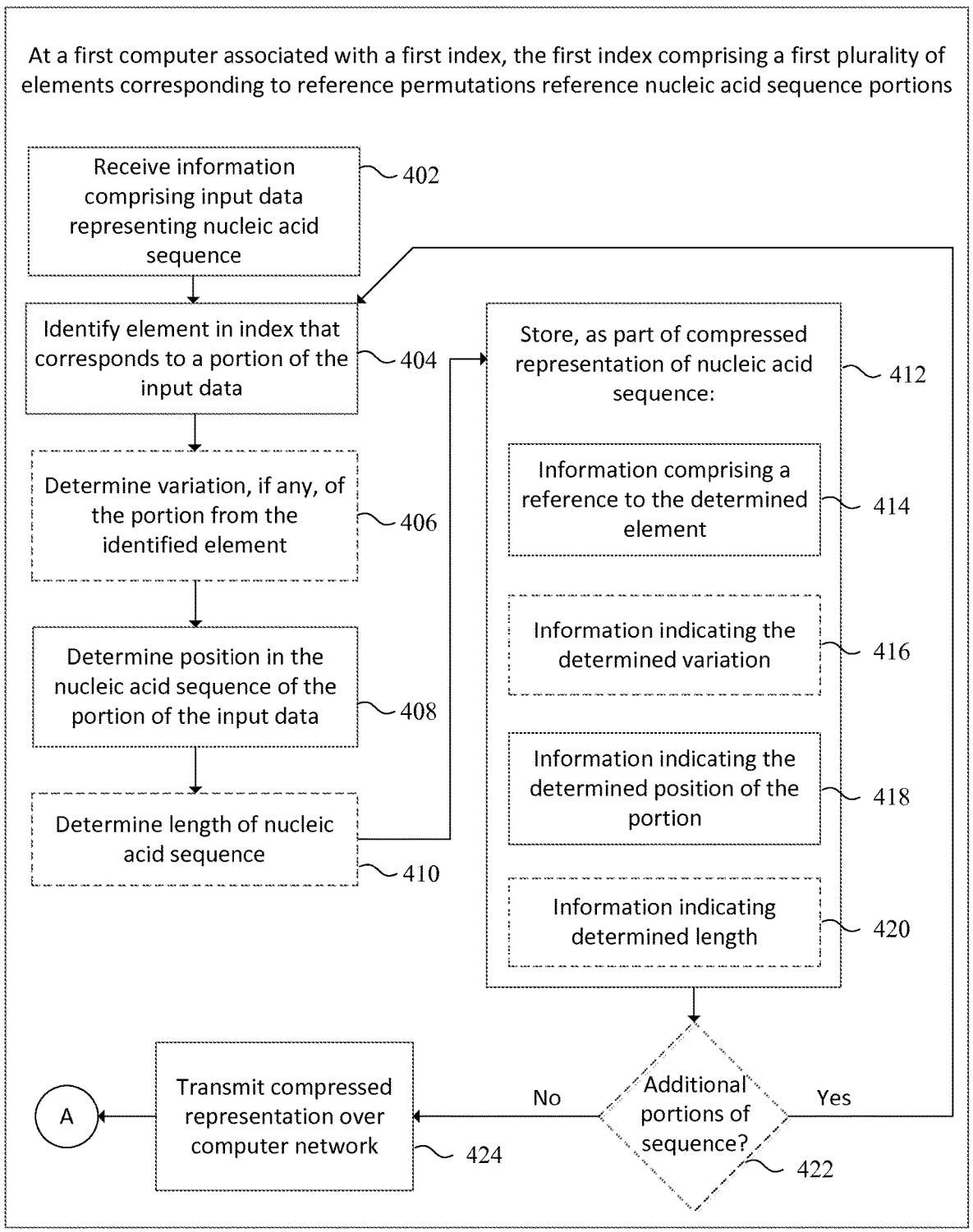
FIGS. 4A and 4B are flow diagrams depicting a method for genomic information compression and transmission.
Figure 4B:
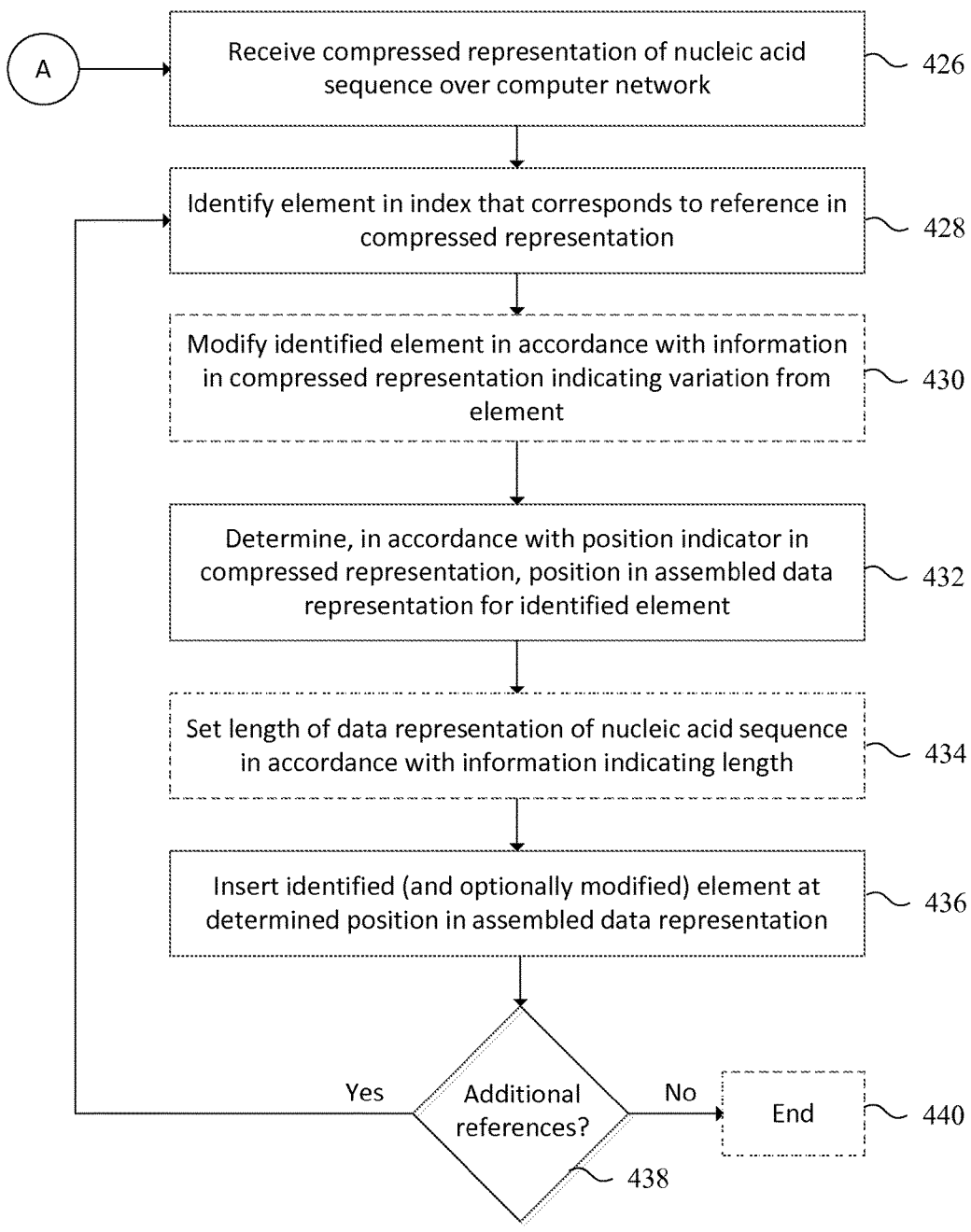

FIGS. 4A and 4B depict a method for compression and transmission of genomic information in accordance with some embodiments. The method 400 may be performed by a system such as the system 100 described above with reference to FIG. 1 and/or the system 300 described above with reference to FIG. 3.

As will be described below, the methods described herein, including exemplary method 400, may achieve efficient compression of genomic information, such that the amount of information sent over a computer network or otherwise communicated from one computer to another is kept small. Instead of transmitting a full-sized representation of the genetic information, the compressed representation may instead be transmitted, and may be used at the receiving end to reconstruct, from the compressed representation and an index, a full-sized representation of the genetic information. In some embodiments, such methods can achieve compression of over 50%, over 75%, over 80%, over 90%, over 95%, over 98%, or over 99%, such that the information transmitted from one computer to another may be much smaller in data size as compared to the full-sized genomic input data originally received at the sending computer and the full-sized, decompressed representation assembled at the receiving computer. Among other advantages, the methods described herein allow for faster and more efficient transmission of genomic information from remote physical locations, including allowing transmission of genomic information via communication mediums (e.g., email) that would not support transmission of uncompressed genomic information.

In some embodiments, some steps of a method are performed at a first computer at a first location (e.g., computer 101a or 302a), while other steps of the method are performed at a second computer at a second location (e.g., computer 101b or 302b). For example, a first computer may compare input genomic information, such as a sequence, to a first index (e.g., index 306a), and may create a compressed representation of the genomic information. The first computer may then transfer the compressed representation to a second computer, such as over a computer network (e.g., network 108 or network 304). The second computer may then compare the compressed representation with a second index (e.g., index 306b), and may assemble a decompressed data representation of the genomic information based on the compressed representation.

In the depicted embodiments of method 400 in FIGS. 4A and 4B, steps 402-424 are performed at a first computer associated with a first index, the first index comprising a first plurality of elements corresponding to reference permutations of nucleic acid sequence portions. Meanwhile, steps 426-438 are performed at a second computer associated with a second index, the second index comprising a second plurality of elements corresponding to reference permutations of nucleic acid sequence portions. In some embodiments, steps 402-424 are performed at computer 101a or 302a, while steps 426-438 are performed at computer 101b or 302b.

At step 402, information comprising input data representing a nucleic acid sequence is received. The input data representing a nucleic acid sequence may be in any suitable and readable format, and may represent any portion of a genomic sequence, including a complete genomic sequence. The input data may be uncompressed, and may exist in any suitable language or character encoding scheme, including, for example, ASCII or UTF-8. The information comprising the input data may be received at the first computer in any suitable manner, including receiving the information over a computerized communication medium (e.g., network communication, communication with physical storage media, manual entry, etc.) and including deriving and/or aligning the information directly (e.g., the input data may be extracted and/or aligned by the same computer that compresses the input data).

In some embodiments, the input data representing a nucleic acid sequence comprises a plurality of portions. For example, a sequence may be several hundred, several thousand, or several million bases in length, and the full sequence may be divisible into a plurality of sub-sequences. The division of a sequence into sub-sequence portions may be done arbitrarily (according to a predefined portion length) or in accordance with patterns recognized in the sequence, such as by aligning the sequence. In some embodiments, the first computer divides the input data, such as a large sequence, into the portions, such as a plurality of sub-sequences. In some embodiments, the portions may be a predefined number of bases in length, such as 16 bases in length. The predefined number of bases that may define the length of a sequence portion may be set in accordance with the number of bases k in the first index and/or the second index. In some embodiments, the portions may be adjacent or non-adjacent, and the portions may be overlapping or non-overlapping.

At step 404, an element in the first index is identified that corresponds to a portion of the input data. The element in the index may be identified in any suitable manner for searching the index and locating an element that is an exact or partial match to the identified portion. In some embodiments, the identified element may be any of the elements "AAAAAAAAAAAAAAAA" (SEQ ID NO: 3) through "CCCCCCCCCCCCCCCC" (SEQ ID NO: 12) such as any one of elements 202a-d in FIG. 2.

In some embodiments, the identified element may be an exact match for the portion; that is, the identified element may be the same k number of bases in length as the portion, and each base in each position may be the same in the element as it is in the portion. In some other embodiments, the identified element may be an inexact match for the portion. That is, one or more of the bases in the portion may not match the identified element, and the identified portion may in some embodiments have more or fewer bases that the number of bases k in the element in the index. In such embodiments in which an imperfect match is identified, an element may be chosen that represents the closest possible match to the portion, such as by having the largest number of identical bases in identical positions.

Optionally, at step 406, a variation is determined, if any, of the identified portion from the identified element. For example, in embodiments such as those explained above in which the identified element is an inexact or imperfect match for the portion, the location, extent, and nature of the variation is determined. In some embodiments, variation of the portion from the nearest possible index element may be due to the index elements not exhaustively covering all possible permutations, or it may be due to an error in the extraction or sequencing of the genetic information. In some embodiments, identifying the variation includes noting the location of the variation, such as the position in the portion or the position in the overall sequence at which the varying base or bases occur. In some embodiments, identifying the variation includes noting whether the portion includes more or fewer bases than the identified element, and, if so, which extra bases or empty positions from the portion correspond to which bases in the identified element. In some embodiments, identifying the variation includes identifying the nucleotides corresponding to the variation, including the nucleotide or nucleotides in the identified element that are not the same as in the portion, and/or the nucleotide or nucleotides in the portion that are not the same as in the identified element. In the case of the portion having extra bases, the nucleotide of each extra base may be noted, and the order of those nucleotides may be noted. In the case of the portion having fewer bases than the identified element, any blank or empty base positions may be noted as blank, empty, uncertain, or as a wildcard.

At step 408, a position in the nucleic acid sequence of the portion of the input data is determined. The position of the portion may be a numeric indicator, such as a numeral, that indicates where the beginning and/or end of the portion is located in relation to the rest of the nucleic acid sequence. In some embodiments, the position may be indicated by a position indicator sharing one or more characteristics with the reference numbers 204 described above with reference to FIG. 2, with the exception that the position data indicates a position at which the permutation represented by the portion manifests in the nucleic acid sequence that is the target of the compression method, rather than (as in FIG. 2) the position data representing the position at which a permutation corresponding to an index element manifests in a reference sequence. For example, a determined position might be "1", which would indicate that the identified portion begins at the first position in the nucleic acid sequence, or it might be "22", which would indicate that the identified portion begins at the 22nd position in the nucleic acid sequence. The convention for denoting the positions relative to one another and relative to the nucleic acid sequence may be set according to any suitable convention.

Optionally, at step 410, a length of the nucleic acid sequence is determined. In some embodiments, the length is the length of the entire nucleic acid sequence. In some embodiments, the length is the length of the entire portion of the nucleic acid sequence to which the first computer has access. In some embodiments, the length is the length of a smaller part of the full sequence, such as the part corresponding to a "read" about which the system is communicating. In some embodiments, the length is expressed in number of elements and/or number of bases, although the length may be expressed in any suitable manner.

At block 412, which contains blocks 414-420, information is stored as part of a compressed representation of the nucleic acid sequence. The information stored at blocks 412-420 may be stored in any suitable storage medium, and may be stored according to any suitable data structure, language, or character encoding scheme. In some embodiments, the data structure used to store several of the pieces of information comprising the compressed representation is substantially smaller in size than the uncompressed input data from which the compressed was derived and/or to which it refers. For example, the compressed representation may comprise an 8-bit reference that refers to a 128-bit element. In some embodiments, pieces of information in the compressed representation may be less than 75% or less, 50% or less, 25% or less, 20% or less, 10% or less, 5% or less, 2% or less, or 1% or less the size of the uncompressed input data from which they were derived and/or to which they refers.

At step 414, information comprising a reference to the determined element is stored as part of the compressed representation of the nucleic acid sequence. In some embodiments, the stored reference comprises a pointer to the corresponding element in the first index that was identified in step 404. The pointer may, for example, be in the form of a reference number. In some embodiments, the reference may be used to look up the corresponding element in the first index, and may also be used to look up corresponding elements having the same reference number in other indexes, such as the second index (e.g., 306*b*) on the second computer (e.g., 302*b* or 101*b*). In some embodiments, the reference may comprise an 8-bit data structure, such as a single integer in ASCII or UTF-8. For example, the reference may be any one of the reference numbers 0 through $4^{k-1}$ shown in FIGS. 2 and 3. In some embodiments, the reference may be a data structure of more than or fewer than 8 bits, for example 16 bits, 32 bits, 64 bits, or 128 bits.

Optionally, at block 416, information indicating the determined variation is stored as part of the compressed representation of the nucleic acid sequence. In some embodiments, the stored indication comprises an indication or functional description of any variation that was determined in step 406. In some embodiments, the stored indication may indicate any of the information discussed above with respect to step 406, including the location and nature of any variation of the portion from the identified element. In some embodiments, the information indicating a determined variation may be 8 bits in size. In some embodiments, the information indicating a determined variation may be more than or fewer than 8 bits in size, for example 16 bits, 32 bits, 64 bits, or 128 bits.

In some embodiments, one variation indication may be stored in the compressed representation for every one reference to an element that is stored, such that every reference has a corresponding variation indicator, or a corresponding indicator that there is no variation. In some other embodiments, including some in which the referenced element represents a perfect match for the portion, there may be less variation indicators in the compressed representation than references to elements in the compressed representation. That is, variation indications may be omitted in some embodiments when there is no variation from an element to indicate. In some embodiments, some references to elements in the compressed representation will have a corresponding variation indication, while other references to elements in the same compressed representation will not.

At block 418, information indicating the determined position of the portion is stored as part of the compressed representation of the nucleic acid sequence. In some embodiments, the information indicating the determined position may comprise any or all of the information discussed above as determined in step 408. In some embodiments, the information indicating the determined position may be stored in the form of position data, such as the position data discussed above with reference to step 408. In some embodiments, the position data may be stored as an integer number, and may be 8 bits in size. In some embodiments, the position data may be more than or fewer than 8 bits in size, for example 16 bits, 32 bits, 64 bits, or 128 bits.

Optionally, at block 420, information indicating the determined length of the nucleic acid sequence may be stored as part of the compressed representation of the nucleic acid sequence. In some embodiments, the information indicating the length may comprise any of the information determined, as discussed above, at step 410. In some embodiments, the information indicating the determined length may be stored only once in the compressed representation of the nucleic acid sequence, which may be advantageous by keeping the size of the compressed representation to a minimum. In some other embodiments, the information indicating the determined length may be stored more than one time, such as one time for each reference to an index element. The latter arrangement, with multiple instances of the length being stored, may be advantageous because it may increase the speed with which the length can be looked up by a computer that receives and analyzes and/or decompresses the compressed representation. In some embodiments, the length may be stored as an integer number, such as representing the number of bases or the number of elements, and may be 8 bits in size. In some embodiments, the length data may be more than or fewer than 8 bits in size, for example 16 bits, 32 bits, 64 bits, or 128 bits.

Optionally, at block 422, it is determined whether there are additional portions of the nucleic acid sequence beyond the one or more portions for which one or more of steps 404-420 have already been carried out. In some embodiments, a computer processor such as processing unit 102*a* determines whether or not there are additional portions of the nucleic acid sequence. In some embodiments, additional portions may be accounted for by sequentially moving down the nucleic acid sequence at any predetermined interval, such as one base at a time or k (the number of bases per element in the first index) bases at a time. In some embodiments, the determination as to whether there are additional portions in the sequence may be made in accordance with an alignment of the sequence, such as an alignment in accordance with any of the techniques disclosed in U.S. application Ser. No. 13/904,738, entitled "Systems and methods for SNP analysis and genome sequencing," which is hereby incorporated by reference.

In some embodiments, the determination as to whether there are any additional portions of the nucleic acid sequence to which steps 404-420 have not yet been carried out may be replaced or supplemented by a determination as to whether there are any additional portions of the sequence for to which steps 404-420 should be carried out. That is, in some embodiments, portions of a nucleic acid sequence to which the compression and transmission method should or should not be applied may be predetermined or actively determined in accordance with any suitable factors, including considering the content of the nucleic acid sequence and/or comparing it to reference nucleic acid sequences. For example, a comparison of the nucleic acid sequence to a reference nucleic acid sequence in order to identify a single nucleotide polymorphism (SNP) (such as in accordance with the techniques disclosed in U.S. application Ser. No. 13/904, 738, entitled "Systems and methods for SNP analysis and genome sequencing.") may be used to determine what portions of the nucleic acid sequence to compress and transmit, such that only portions in a predetermined vicinity of the SNP may be compressed and transmitted.

If it is determined at step 422 that there are one or more additional portions of the nucleic acid sequence to which the compression method (e.g., steps 404-420) has not yet been applied and to which the compression method should be applied, then the method returns to step 404 and iterate by proceeding with respect to a next portion. If, however, it is determined that there are no additional portions of the nucleic acid sequence to which the compression method has not yet been applied or that there are no additional portions of the nucleic acid sequence to which the compression method should be applied, then the method proceeds to step 424.

At step 424, the compressed representation of the nucleic acid sequence is transmitted over a computer network. The compressed representation of the nucleic acid sequence may contain any of the information discussed above with respect to steps 404-420, as well as additional information. The compressed representation of the nucleic acid sequence may contain information regarding a single portion of the nucleic acid sequence, or it may contain information regarding a plurality of portions of a nucleic acid sequence. For example, the compressed representation may contain some of all of the pieces of information discussed with respect to steps 414-420, and it may contain one instance of each type of that information (e.g., one reference to an element, one variation indication, one location indication, etc.) with respect to each portion of the nucleic acid sequence for which the compression method (e.g., steps 404-420) was iteratively applied. In embodiments in which the compressed representation contains information regarding a plurality of portions, the pieces of information regarding each portion may be arranged, structured, or tagged in such a manner such that they can be correlated with other pieces of information pertaining to the same portion. For example, a reference to an element corresponding to a first portion may be tagged, arranged, or structured such that it may be identified as corresponding with a location indication that also corresponds to the first portion.

The compressed representation may be transmitted according to any suitable protocol by which information may be transmitted over a computer network. The compressed representation may be divided and sent in multiple distinct data structures and/or multiple transmissions (e.g., as multiple files), or it may be sent as one cohesive data structure and/or one transmission (e.g., as one file). In some embodiments, the information respecting multiple portions of the nucleic acid sequence may be sent as a single transmission and/or a single data structure, while in other embodiments the information respecting each distinct portion of the nucleic acid sequence may be sent as a distinct transmission and/or a distinct data structure. In some embodiments, the compressed representation may be sent via email, including as an email attachment.

In some embodiments, the compressed representation may be transmitted from one computer to another and/or from one location to another by a method other than computer network transmission. For example, in some embodiments, the compressed representation may be transmitted from a first computer by transferring the information on a physical drive (e.g., a flash drive or a portable hard drive).

FIG. 4B depicts a continuation of the method depicted in FIG. 4A. At step 426, method 400 continues after step 424 in FIG. 4A.

In the depicted embodiments of method 400 in FIG. 4B, steps 426-438 are performed at a second computer associated with a second index, the second index comprising a second plurality of elements corresponding to reference permutations of nucleic acid sequence portions. In some embodiments, the second index is the same as the first index, such that each index contains the same elements with the same corresponding reference numbers. In some embodiments, steps 426-438 are performed at computer 101*b* or 302*b*.

At step 426, the compressed representation of the nucleic acid sequence is received over the computer network. In some other embodiments, such as (but not limited to) embodiments in which the compressed representation was transmitted from the first computer by means other than transmission over a computer network, the compressed representation is received by the second computer by means other than by receipt from a computer network. For example, in some embodiments, the compressed representation may be received by the second computer by transferring the information on a physical drive (e.g., a flash drive or a portable hard drive).

At step 428, an element that corresponds to a reference in the compressed representation is identified in the second index. In some embodiments, the reference is used to look up, identify, and retrieve the element from the second index, such as by locating the reference number in the second index and reading the corresponding element. In some embodiments in which the second index reflects the same elements and same corresponding reference numbers as the first index, this element retrieval process will result in the same element being retrieved from the second index as was used to create the compressed representation with respect to the instant portion at the first index.

Optionally, at step 430, the element identified in the second index is modified in accordance with information in the compressed representation indicating variation from the corresponding referenced element. In some embodiments, information indicating a variation from a corresponding element is read from the compressed representation, and the information is applied in order to modify the corresponding element that has been retrieved from the second index. The modifications made to the second element may reflect any or all of the variations noted in the compressed representation, including any or all of the kinds of variations discussed above with respect to steps 406 and 416. For example, if the information indicating a variation indicates that a certain nucleotide in a particular element actually corresponds to a different nucleotide in the original portion, to multiple nucleotides in the original portion, or to a blank, uncertain, or wildcard base in the original portion, then the nucleotide in the retrieved element may be modified to reflect the change. In this way, after the modification, the retrieved element may reflect the original portion more closely, including by reflecting any variations noted in the compressed representation.

At step 432, a corresponding position in an assembled data representation of the nucleic acid sequence is determined in accordance with a position indicator in the compressed representation that corresponds to the referenced element. The assembled data representation of the nucleic acid sequence may be a "decompressed" data representation of the nucleic acid sequence that is created by assembling elements of the second index that are referenced by references in the compressed representation. In some embodiments, the assembled data representation is an exact recreation or reconstruction of the input data that was compressed by the first computer, or some portion thereof (or it is a recreation or reconstruction with a small number of differences, such as differences represented by a small number of bases, such as less than 10, less than five, or one). In some embodiments, the assembled data representation is an exact recreation of the same data structure and data format in which the input data existed on the first computer, while in some embodiments the assembled data representation is in a different file format and/or a different data structure. In some embodiments, the assembled data representation is the same size as the input data representing the nucleic acid sequence, while in some other embodiments it may be either larger or smaller than the input data.

In some embodiments, the assembled data representation can be understood as having "positions" or "locations" in the same manner that the input data representing the nucleic acid sequence has positions or locations for each portion thereof. In some embodiments, at step 432, a position is determined in accordance with information in the compressed representation indicating a position of a corresponding element indicated by a reference in the compressed representation. For example, the second computer may read position data, as discussed above with respect to steps 408 and 418, from the compressed representation.

Optionally, at step 434, a length of the data representation of the nucleic acid sequence is set in accordance with information in the compressed representation indicating a length. As explained above, the data representation of the nucleic acid sequence may be a "decompressed" data representation of the nucleic acid sequence that is created by assembling elements of the second index that are referenced by references in the compressed representation. In some embodiments, the length of the data representation may be set or modified in accordance with information in the compressed representation indicating a length, as determined and stored in accordance with steps 410 and 420 as discussed above. For example, the second computer may read the information indicating a length from the compressed representation, such as a number of bases or a number of elements, and may set or modify the number of bases or the number of elements of the data representation in accordance with the number of bases or elements indicated in the compressed representation.

As discussed above with respect to step 420, in some embodiments, the compressed representation of a nucleic acid sequence includes only one length indication, while in other embodiments, the compressed representation includes multiple length indications. In some embodiments, all of the multiple length indications in a single compressed representation may be the same, but in some embodiments the indications may be different. In some embodiments in which there is only one length indication, the length may be set only once regardless of the number of times that the decompression method (e.g., steps 428-436) is iterated. In some embodiments in which there is more than one length indication, the length may be set only once, for example upon a first iteration. In other embodiments in which there is more than one length indication, the length may be set multiple times upon multiple iterations, such as when a new iteration indicates that the length should be changed.

At step 436, the identified and optionally modified element is inserted at the determined position into the assembled data representation. In some embodiments, the element that is identified and retrieved from the second index in step 428 and optionally modified at step 430 is inserted in at the position determined in step 432. In this manner, for example, a 16-base element may be retrieved from index 2, modified by changing the last base in the element to different nucleotide, and inserted after the modification into the first position in the assembled data representation; thus, the first 15 bases of the assembled data representation may reflect the first 15 bases of the identified element from the second index, and the $16^{th}$ base may reflect the nucleotide variation indicated in the compressed representation. In some embodiments, the first 16 bases of the assembled representation may exactly or nearly-exactly match the first 16 bases of the input data.

At step 438, it is determined whether there are additional references in the compressed representation beyond the one or more references for which one or more of steps 428-436 have already been carried out. In some embodiments, a computer processor such as processing unit 102b determines whether or not there are additional references in the compressed representation. In some embodiments, additional representations may be accounted for by sequentially moving through the data in the compressed representation.

If it is determined at step 438 that there are one or more additional references in the compressed representation to which the decompression method (e.g., steps 428-436) has not yet been applied and to which the decompression method should be applied, then the method returns to step 428 and iterated by proceeding with respect to a next element. If, however, it is determined that there are no additional elements in the compressed representation to which the decompression method has not yet been applied or that there are no additional elements in the compressed representation to which the decompression method should be applied, then the method proceeds to step 440.

Optionally, at step 440, the method 400 ends. At the completion of the method after step 440, in some embodiments, a decompressed data representation of the nucleic acid sequence has been assembled on the second computer, wherein the decompressed data representation mirrors the input data that was compressed on the first computer. In some embodiments, both the input data and the decompressed data representation, which may be identical or substantially identical, comprise substantially more data (e.g., they are substantially larger in size, such as 2× larger or more, 5× larger or more, 10× larger or more, 20× larger or more, 25× larger or more, 50× larger or more, 75× larger or more, 98× larger or more, or 99× larger or more) than the compressed representation that was transmitted from the first computer to the second computer.

Single Nucleotide Polymorphism Compression

Attention is now directed to embodiments in which a compressed representation of one or more polymorphisms, such as single nucleotide polymorphisms (SNPs), is created and transmitted. In some such embodiments, the compression and transmission may be carried out with similar systems and indexes as described above, with an exception that the method may include aligning and comparing the input nucleic acid data with a reference nucleic acid sequence at the first computer. The reference nucleic acid sequence may be stored on the first computer in any suitable manner, including being stored in an index having position data stored therein describing the reference sequence, as described in FIG. 2 and in U.S. application Ser. No. 13/904,738, entitled "Systems and methods for SNP analysis and genome sequencing." For example, the first computer may align and compare the input nucleic acid sequence to the stored reference nucleic acid sequence to identify differences, such as SNPs, between the input nucleic acid sequence and the reference sequence. After identifying the SNPs, a compressed representation of the differences alone (e.g., of the polymorphism(s)), may be sent from the first computer to the second computer, rather than sending a compressed representation of the entire nucleic acid sequence including the parts that are not different from the reference sequence. In some embodiments, the second computer has a stored representation of the reference sequence, which may be identical to the reference sequence stored on the first computer. The second computer may then access the stored reference sequence and use the compressed SNP representation to apply modifications to the reference sequence to reconstruct the input sequence having the SNPs identified by the first computer.

When creating a compressed representation of a polymorphism, the compressed representation may include the following data: (1) data indicating a position or location at which a polymorphism manifests, such as a location in a sequence at which a polymorphism manifests; (2) data indicating a variation, such as the variation information described above with reference to step 406, of the input data from a reference nucleic acid sequence; and (3) data indicating a strand in which the polymorphism manifests. In some embodiments, data indicating a polymorphism such as a single nucleotide polymorphism may be represented by a compressed representation that is 8 bits in size, representing a 70% compression from its original size.

In some embodiments, both the input data and the decompressed data representation of the nucleic acid sequence, which may be identical or substantially identical, comprise substantially more data (e.g., they are substantially larger in size, such as 2× larger or more, 5× larger or more, 10× larger or more, 20× larger or more, 25× larger or more, 50× larger or more, 75× larger or more, 98× larger or more, or 99× larger or more) than the compressed representation indicating the identified SNPs.

In some embodiments, a compressed representation of a polymorphism in accordance with the compression method described above may be included in the compressed representation of a nucleic acid sequence as described above with respect to method 400. In some embodiments, a compressed representation of a polymorphism may be transmitted as a stand-alone piece of data.

Although this application gives examples of the sizes of various data structures (including in the disclosures above and the examples below), the sizes used are merely exemplary, and are not intended to be limiting. Other data sizes may be used.

EXAMPLE 1

In a future embodiment, the following structure is used to form part of a compressed representation of a nucleic acid sequence. The following data structures are used with two identical instances of an index that each contain every possible permutation of 16-base elements comprised of nucleotides A, T, C, and G. Each index will contain $4^k$ 128-bit elements, each element associated with an 8-bit reference number 0 through $4^{k-1}$.

The following structure represents a compressed data structure for representing a sequence portion for which the elements in the first and second index are capable of expressing an exact match. That is, when the elements in the indexes can be used to assemble an exact representation of the portion, the following compressed data structure is used.

```
typedef struct CompressedReads
{
    uint16_t referenceId;
    uint32_t referenceLoc;
    uint16_t readLen;
} CompressedRead;
```

In this structure, "referenceId" represents a reference to an element in an index, the element corresponding to the portion, in the form of an integer reference number between 0 and $4^{k-1}$. The reference numbers are 16 bits in size.

In this structure, "referenceLoc" represents position data, which is information indicating a position or location in the nucleic acid sequence at which the element referenced by the "referenceId" is located in the sequence. The position data is 16 bits in size.

In this structure, "readLen" represents a length of the nucleic acid sequence or a part of the sequence. The information representing the length is 16 bits in size.

The following structure represents a compressed data structure for representing a sequence portion for which the elements in the first and second index are not capable of expressing an exact match. That is, when the elements in the indexes cannot be used to assemble an exact representation of the portion, the following compressed data structure is used.

```
typedef struct CompressedImperfectReads
{
    uint32_t readId;
    uint16_t referenceId;
    uint32_t referenceLoc;
    uint16_t readLen;
} CompressedImperfectRead;
```

In this structure, the same "referenceId," "referenceLoc," and "referenceLen" components as described above are included.

In this structure, "readId" represents information indicating a variation of the portion from the element indicated by "referenceId." The information representing the variation is 8 bits in size.

The following structure represents a compressed data structure for representing a single nucleotide polymorphism (SNP).

```
typedef struct CompressedSNPs
{
    uint16_t readLoc;
    uint32_t readId;
    char allele;
} CompressedSNP;
```

In this structure, the same "readId" component as described above is included, and will describe the variation from a reference sequence, the variation constituting the SNP. The information representing the variation is 8 bits in size.

In this structure, "readLoc" represents position data, which is information indicating a position or location, such as a position or location in a nucleic acid sequence, at which the SNP is located. The position data is 8 to 16 bits in size.

In this structure, "char allele" represents a strand at which the SNP indicated by the variation described by "readId" is manifested. The information representing the strand is 8 bits in size.

EXAMPLE 2

In a future embodiment, the genome of *E. coli* is represented by input data that is approximately 5 GB in size. Using the compression methodology described above with indexes having $4^k$ 128-bit elements, each element associated with an 8-bit reference number 0 through $4^{k-1}$, the *E. coli* genome is compressed to 357.14 MB in size, and is transmitted via a computer network from one computer to another for decompression. This compression is a compression to approximately 7% of the original size of the input data.

What is claimed is:

1. A method for communicating compressed genomic information, comprising:
    receiving information comprising input data representing a nucleic acid sequence, wherein the nucleic acid sequence is an entire genome and the received information comprises one or more nucleotide base indicators and one or more wildcard base indicators;
    identifying a plurality of portions in the input data, wherein each portion of the plurality of portions comprises a predetermined number of sequential bases, wherein the predetermined number is equal to or greater than 8, and wherein identifying the plurality of portions comprises sequentially moving along the nucleic acid sequence by one base at a time;
    identifying, for each of the plurality of portions, an element in an index that corresponds to the respective portion, wherein the index comprises a plurality of elements corresponding to reference permutations of nucleic acid sequence portions, wherein the index comprises one element each for every mathematically possible permutation of four bases and a wildcard base indicator for nucleic acid sequence portions of the predetermined number of bases;
    determining, for each of the plurality of portions, a position in the nucleic acid sequence of the respective portion;
    storing, for each of the plurality of portions, as part of a compressed representation of the nucleic acid sequence, information comprising a reference to the respective identified element, and information indicating the determined position of the respective portion, wherein the compressed representation does not include the index; and
    transmitting the compressed representation of the nucleic acid sequence over a computer network.

2. The method of claim 1, further comprising:
    determining, for one or more of the plurality of portions, a variation from the corresponding element; and
    storing, for each of the one or more plurality of portions, as part of a compressed representation of the nucleic acid sequence, information indicating the determined variation.

3. The method of claim 1, further comprising:
    determining a length of the data representing the nucleic acid sequence; and
    storing, as part of a compressed representation of the nucleic acid sequence, information indicating the determined length.

4. The method of claim 1, further comprising:
    identifying, in one or more of the plurality of portions, a polymorphism; and
    storing, as part of a compressed representation of the nucleic acid sequence, information indicating a strand in which the polymorphism is manifested.

5. The method of claim 1, wherein the nucleic acid sequence comprises one of DNA, cDNA, RNA, mRNA, or PNA.

6. The method of claim 1, wherein a number of bases in one or more of the elements of the plurality of elements is 16.

7. The method of claim 1, wherein the compressed representation is less than 75% of the size of the input data.

8. The method of claim 1, wherein:
    the index comprises one or more elements corresponding to reference permutations of nucleic acid sequences indicated by one or more databases associated with the index to be associated with a first species, and
    the index comprises one or more elements corresponding to reference permutations indicated by one or more databases associated with the index to be associated with a second species.

9. The method of claim 1, wherein the index comprises one or more elements indicated by one or more databases associated with the index as not being associated with any species.

10. A method of receiving compressed genomic information, comprising:
    receiving a compressed representation of a nucleic acid sequence over a computer network, wherein the compressed representation represents the nucleic acid sequence as a plurality of portions, wherein each portion of each portion of the plurality of portions comprises a predetermined number of sequential bases, wherein the predetermined number is equal to or greater than 8, and wherein the nucleic acid sequence is an entire genome;
    identifying, in accordance with each of a plurality of references in the compressed representation, a corresponding respective element in an index, wherein the index comprises a plurality of elements corresponding to reference permutations of nucleic acid sequences portions, wherein the compressed representation does not include the index, wherein the index comprises one element each for every mathematically possible permutation of four bases and a wildcard base indicator for nucleic acid sequence portions of the predetermined number of bases;
    determining, in accordance with each of a plurality of indicators in the compressed representation, a respective position in an assembled data representation for each identified element; and
    assembling the data representation of the nucleic acid sequence by inserting each identified element at the corresponding determined position, wherein the assembled data representation comprises one or more nucleotide base indicators and one or more wildcard base indicators.

11. The method of claim 10, further comprising:
    modifying one or more of the identified elements in accordance with information in the compressed representation indicating a variation from one of the one or more identified elements.

12. The method of claim 10, further comprising:
    setting a length of the data representation of the nucleic acid sequence in accordance with information, in the compressed representation, indicating the length.

13. The method of claim 10, further comprising:
    inserting a representation of a polymorphism into the data representation of the nucleic acid sequence in accordance with information, in the compressed representation, indicating a strand at which the polymorphism is manifested.

14. The method of claim 10, wherein:
    the index comprises one or more elements corresponding to reference permutations of nucleic acid sequences indicated by one or more databases associated with the index to be associated with a first species, and
    the index comprises one or more elements corresponding to reference permutations indicated by one or more databases associated with the index to be associated with a second species.

15. The method of claim 10, wherein the index comprises one or more elements indicated by one or more databases associated with the index as not being associated with any species.

16. A method for communicating compressed genomic information, comprising:
    at a first computer associated with a first index, wherein the first index comprises a first plurality of elements corresponding to reference permutations of nucleic acid sequence portions, wherein the first index comprises one element each for every mathematically possible permutation of four bases and a wildcard base indicator for nucleic acid sequence portions of a predetermined number of bases:
    receiving information comprising input data representing a nucleic acid sequence, wherein the nucleic acid sequence is an entire genome and the received information comprises one or more nucleotide base indicators and one or more wildcard base indicators;
    identifying a plurality of portions in the input data, wherein each portion of the plurality of portions comprises the predetermined number of sequential bases, wherein the predetermined number is equal to or greater than 8, and wherein identifying the plurality of portions comprises sequentially moving along the nucleic acid sequence by one base at a time;
    identifying, for each of the plurality of portions, an element in the first index that corresponds to the respective portion;
    determining, for each of the plurality of portions, a position in the nucleic acid sequence of the respective portion;
    storing, for each of the plurality of portions, as part of a compressed representation of the nucleic acid sequence information comprising a reference to the respective identified element, and information indicating the determined position of the respective portion, wherein the compressed representation does not include the index; and
    transmitting the compressed representation of the nucleic acid sequence over a computer network;
    at a second computer associated with a second index, wherein the second index comprises a second plurality of elements corresponding to reference permutations of nucleic acid sequence portions, wherein the second index comprises one element each for every mathematically possible permutation of four bases and a wildcard base indicator for nucleic acid sequence portions of the predetermined number of bases;
    receiving the compressed representation of the nucleic acid sequence over the computer network;
    identifying, in accordance with each of the plurality of references in the compressed representation, a corresponding respective element in the second index;
    determining, in accordance with each of a plurality of indicators in the compressed representation, a respective position in an assembled data representation for each identified element; and
    assembling the data representation of the nucleic acid sequence by inserting each identified element at the corresponding determined position, wherein the assembled data representation comprises one or more nucleotide base indicators and one or more wildcard base indicators.

17. The method of claim 16, wherein the first plurality of elements and the second plurality of elements represent the same reference permutations of nucleic acid sequence portions.

18. The method of claim 16, wherein:
    the first and second index each comprise one or more elements corresponding to reference permutations of nucleic acid sequences indicated by one or more databases associated with the index to be associated with a first species, and the first and second index each comprise one or more elements corresponding to reference permutations indicated by one or more databases associated with the index to be associated with a second species.

19. The method of claim 16, the first and second index each comprise one or more elements indicated by one or more databases associated with the index as not being associated with any species.

20. A system for communicating compressed genomic information, comprising:
a first computer having a memory having stored thereon a first index, the first index comprising a first plurality of elements corresponding to reference permutation of nucleic acid sequence portions, wherein the first index comprises one element each for every mathematically possible permutation of four bases and a wildcard base indicator for nucleic acid sequence portions of a predetermined number of bases, wherein the predetermined number is equal to or greater than 8;
a second computer having a memory having stored thereon a second index, the second index comprising a second plurality of elements corresponding to reference permutations of nucleic acid sequence portions, wherein the second index comprises one element each for every mathematically possible permutation of four bases and a wildcard base indicator for nucleic acid sequence portions of the predetermined number of bases;
a network enabling data to be transferred from the first computer to the second computer; and
a first processor associated with the first computer, the first processor configured to:
receive information comprising input data representing a nucleic acid sequence, wherein the nucleic acid sequence is an entire genome and the received information comprises one or more nucleotide base indicators and one or more wildcard base indicators;
identify a plurality of portions in the input data, wherein each portion of the plurality of portions comprises a predetermined number of sequential bases, wherein identifying the plurality of portions comprises sequentially moving along the nucleic acid sequence by one base at a time;
identify, for each of the plurality of portions, an element in the first index that corresponds to the respective portion;
determine, for each of the plurality of portions, a position in the nucleic acid sequence of the respective portion;
store, for each of the plurality of portions, as part of a compressed representation of the nucleic acid sequence information comprising a reference to the respective identified element, and information indicating the determined position of the respective determined portion, wherein the compressed representation does not include the index; and
transmit the compressed representation of the nucleic acid sequence over a computer network;
a second processor associated with the second computer, the second processor configured to:
receive the compressed representation of the nucleic acid sequence over the computer network;
identify, in accordance with each of the plurality of references in the compressed representation, a corresponding respective element in the second index;
determine, in accordance with each of a plurality of indicators in the compressed representation, a respective position in an assembled data representation for each identified element; and
assemble the data representation of the nucleic acid sequence by inserting each identified element at the corresponding determined position, wherein the assembled data representation comprises one or more nucleotide base indicators and one or more wildcard base indicators.

21. The system of claim 20, wherein:
the first and second index each comprise one or more elements corresponding to reference permutations of nucleic acid sequences indicated by one or more databases associated with the index to be associated with a first species, and
the first and second index each comprise one or more elements corresponding to reference permutations indicated by one or more databases associated with the index to be associated with a second species.

22. The system of claim 20, the first and second index each comprise one or more elements indicated by one or more databases associated with the index as not being associated with any species.

* * * * *

SEQUENCE LISTING

<160> NUMBER OF SEQ ID NOS: 18

<210> SEQ ID NO 1
<211> LENGTH: 16
<212> TYPE: DNA
<213> ORGANISM: Unknown
<220> FEATURE:
<223> OTHER INFORMATION: exemplary construct

<400> SEQUENCE: 1
gtaagatccg ctacaa                                                    16

<210> SEQ ID NO 2
<211> LENGTH: 23
<212> TYPE: DNA
<213> ORGANISM: Unknown
<220> FEATURE:
<223> OTHER INFORMATION: exemplary construct

<400> SEQUENCE: 2
atccgctaat gcgccgtagt ccg                                            23

<210> SEQ ID NO 3
<211> LENGTH: 16
<212> TYPE: DNA
<213> ORGANISM: Unknown
<220> FEATURE:
<223> OTHER INFORMATION: exemplary construct

<400> SEQUENCE: 3
aaaaaaaaaa aaaaaa                                                    16

<210> SEQ ID NO 4
<211> LENGTH: 16
<212> TYPE: DNA
<213> ORGANISM: Unknown
<220> FEATURE:
<223> OTHER INFORMATION: exemplary construct

```
<400> SEQUENCE: 4
aaaaaaaaaa aaaaat                                                    16

<210> SEQ ID NO 5
<211> LENGTH: 16
<212> TYPE: DNA
<213> ORGANISM: Unknown
<220> FEATURE:
<223> OTHER INFORMATION: exemplary construct

<400> SEQUENCE: 5
aaaaaaaaaa aaaata                                                    16

<210> SEQ ID NO 6
<211> LENGTH: 16
<212> TYPE: DNA
<213> ORGANISM: Unknown
<220> FEATURE:
<223> OTHER INFORMATION: exemplary construct

<400> SEQUENCE: 6
aaaaaaaaaa aaaatt                                                    16

<210> SEQ ID NO 7
<211> LENGTH: 16
<212> TYPE: DNA
<213> ORGANISM: Unknown
<220> FEATURE:
<223> OTHER INFORMATION: exemplary construct

<400> SEQUENCE: 7
gtaagatccg ctacat                                                    16

<210> SEQ ID NO 8
<211> LENGTH: 16
<212> TYPE: DNA
<213> ORGANISM: Unknown
<220> FEATURE:
<223> OTHER INFORMATION: exemplary construct

<400> SEQUENCE: 8
gtaagatccg ctacta                                                    16

<210> SEQ ID NO 9
<211> LENGTH: 16
<212> TYPE: DNA
<213> ORGANISM: Unknown
<220> FEATURE:
<223> OTHER INFORMATION: exemplary construct

<400> SEQUENCE: 9
cgcccccccc ccccg                                                     16

<210> SEQ ID NO 10
<211> LENGTH: 16
<212> TYPE: DNA
<213> ORGANISM: Unknown
<220> FEATURE:
<223> OTHER INFORMATION: exemplary construct

<400> SEQUENCE: 10
cgcccccccc ccccgc                                                    16

<210> SEQ ID NO 11
```

```
<211> LENGTH: 16
<212> TYPE: DNA
<213> ORGANISM: Unknown
<220> FEATURE:
<223> OTHER INFORMATION: exemplary construct

<400> SEQUENCE: 11
cgcccccccc cccccc                                                      16

<210> SEQ ID NO 12
<211> LENGTH: 16
<212> TYPE: DNA
<213> ORGANISM: Unknown
<220> FEATURE:
<223> OTHER INFORMATION: exemplary construct

<400> SEQUENCE: 12
cccccccccc cccccc                                                      16

<210> SEQ ID NO 13
<211> LENGTH: 13
<212> TYPE: DNA
<213> ORGANISM: Unknown
<220> FEATURE:
<223> OTHER INFORMATION: exemplary construct

<400> SEQUENCE: 13
cgcccccccc ccg                                                         13

<210> SEQ ID NO 14
<211> LENGTH: 13
<212> TYPE: DNA
<213> ORGANISM: Unknown
<220> FEATURE:
<223> OTHER INFORMATION: exemplary construct

<400> SEQUENCE: 14
cgcccccccc cgc                                                         13

<210> SEQ ID NO 15
<211> LENGTH: 13
<212> TYPE: DNA
<213> ORGANISM: Unknown
<220> FEATURE:
<223> OTHER INFORMATION: exemplary construct

<400> SEQUENCE: 15
cgcccccccc ccc                                                         13

<210> SEQ ID NO 16
<211> LENGTH: 13
<212> TYPE: DNA
<213> ORGANISM: Unknown
<220> FEATURE:
<223> OTHER INFORMATION: exemplary construct

<400> SEQUENCE: 16
cccccccccc ccc                                                         13

<210> SEQ ID NO 17
<211> LENGTH: 16
<212> TYPE: DNA
<213> ORGANISM: Unknown
<220> FEATURE:
<223> OTHER INFORMATION: exemplary construct

<400> SEQUENCE: 17
```

```
attgcttcca tgggtc                                                          16
```

```
<210> SEQ ID NO 18
<211> LENGTH: 108
<212> TYPE: PRT
<213> ORGANISM: Unknown
<220> FEATURE:
<223> OTHER INFORMATION: exemplary construct

<400> SEQUENCE: 18

Asp Val Gln Met Ile Gln Ser Pro Ser Ser Leu Ser Ala Ser Leu Gly
1               5                   10                  15

Asp Ile Val Thr Met Thr Cys Gln Ala Ser Gln Gly Thr Ser Ile Asn
            20                  25                  30

Leu Asn Trp Phe Gln Gln Lys Pro Gly Lys Ala Pro Lys Leu Leu Ile
            35                  40                  45

Tyr Gly Ser Ser Asn Leu Glu Asp Gly Val Pro Ser Arg Phe Ser Gly
        50                  55                  60

Ser Arg Tyr Gly Thr Asp Phe Thr Leu Thr Ile Ser Ser Leu Glu Asp
65                  70                  75                  80

Glu Asp Leu Ala Thr Tyr Phe Cys Leu Gln His Ser Tyr Leu Pro Tyr
                85                  90                  95

Thr Phe Gly Gly Gly Thr Lys Leu Glu Ile Lys Arg
                100                 105
```